(12) United States Patent
Takemura et al.

(10) Patent No.: US 11,945,791 B2
(45) Date of Patent: Apr. 2, 2024

(54) ALLYL COMPOUND AND COMPOSITION FOR OPTICAL MATERIAL

(71) Applicant: MITSUBISHI GAS CHEMICAL COMPANY, INC., Tokyo (JP)

(72) Inventors: Kouhei Takemura, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 660 days.

(21) Appl. No.: 17/264,018

(22) PCT Filed: Aug. 1, 2019

(86) PCT No.: PCT/JP2019/030111
§ 371 (c)(1),
(2) Date: Jan. 28, 2021

(87) PCT Pub. No.: WO2020/031815
PCT Pub. Date: Feb. 13, 2020

(65) Prior Publication Data
US 2021/0292297 A1    Sep. 23, 2021

(30) Foreign Application Priority Data
Aug. 8, 2018    (JP) ................. 2018-149374

(51) Int. Cl.
*C07D 331/02*    (2006.01)
*C08G 75/08*    (2006.01)
*G02B 1/04*    (2006.01)

(52) U.S. Cl.
CPC .......... *C07D 331/02* (2013.01); *C08G 75/08* (2013.01); *G02B 1/041* (2013.01)

(58) Field of Classification Search
None
See application file for complete search history.

(56) References Cited

U.S. PATENT DOCUMENTS 5,807,975 A    9/1998    Amagai et al.
6,225,439 B1    5/2001    Amagai et al.

FOREIGN PATENT DOCUMENTS

| EP | 0 980 696 A1 | 2/2000 |
|----|--------------|--------|
| JP | 9-71580 A | 3/1997 |
| JP | 9-110979 A | 4/1997 |
| JP | 11-166037 A | 6/1999 |
| JP | 2001-163878 A | 6/2001 |

OTHER PUBLICATIONS

Extended European Search Report issued in European Patent Application No. 19847478.5 dated Sep. 21, 2021.
H.J. Backer et al., "Les Thioethers Du Pentaerythritol", Recueil des Travaux Chimiques des Pays-Bas et de la Belgique, vol. 51, 1932, pp. 2899-293, cited in ISR.
International Search Report issued in International Patent Application No. PCT/JP2019/030111, dated Oct. 1, 2019, along with an English translation thereof.
Written Opinion of the International Searching Authority issued in International Patent Application No. PCT/JP2019/030111, dated Oct. 1, 2019, along with an English translation thereof.

*Primary Examiner* — Megan McCulley
(74) *Attorney, Agent, or Firm* — GREENBLUM & BERNSTEIN, P.L.C.

(57) ABSTRACT

The present invention makes it possible to provide a compound represented by formula (1) and a composition for an optical material containing this compound.

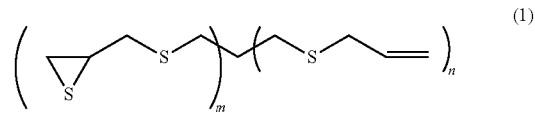

(Where m+n=4, m represents an integer of from 0 to 3, and n represents an integer of from 1 to 4.) In addition, the present invention makes it possible to provide a method for producing an optical material, the method including a step for adding 0.0001-10 parts by mass of a polymerization catalyst per 100 parts by mass of the composition for an optical material, polymerizing, and curing.

4 Claims, No Drawings

ALLYL COMPOUND AND COMPOSITION FOR OPTICAL MATERIAL

TECHNICAL FIELD

The present invention relates to an allyl compound which can favorably be used as an optical material such as a plastic lens, a prism, an optical fiber, an information recording medium and a filter, particularly, a plastic lens.

BACKGROUND ART

Plastic lenses are lightweight, tough and can easily be dyed. Performance that are particularly required for plastic lenses include low specific gravity, high transparency and low yellowness, optical performance such as high refractive index and high Abbe number, high heat resistance, high strength and the like. High refractive index allows reduction of the lens thickness while high Abbe number can reduce chromatic aberration of the lens.

One of the most widely used resins for application to plastic lenses is diethylene glycol bis(allyl carbonate). While this resin has superior dyeability and workability, its refractive index is as low as 1.50 and thus the resulting lens becomes thick. Therefore, a material with a higher refractive index has been needed.

Recently, a number of organic compounds having a sulfur atom have been proposed for the purpose of earning a high refractive index and a high Abbe number. Among them, a linear polyepisulfide compound having a sulfur atom not only has a refractive index that exceeds 1.7, but is also known to have a well-balanced Abbe number (Patent document 1).

Plastic lenses produced from such an episulfide compound, however, have poor dyeability, and thus productivity of the lenses was decreased in some cases. In order to improve dyeability, addition of a compound having an active hydrogen group (Patent document 2), an allyl compound (Patent document 3) and else have been proposed. When such compounds were added in order to earn a sufficient dyeability, heat resistance of the resin was deteriorated and thus workability for secondary processing such as coating or the like sometimes became poor.

PRIOR ART DOCUMENTS

Patent Documents

Patent document 1: Japanese Unexamined Patent Application Publication No. H09-110979
Patent document 2: Japanese Unexamined Patent Application Publication No. H11-166037
Patent document 3: Japanese Unexamined Patent Application Publication No. 2001-163878

SUMMARY OF THE INVENTION

Problems to be Solved by the Invention

The present invention has an objective of providing an optical material with a high refractive index, which has enhanced dyeability without its heat resistance being deteriorated.

Means for Solving the Problems

Under such circumstances, the present inventors have gone through extensive studies and solved this problem with an allyl compound having a particular structure containing an episulfide group, and a composition for an optical material comprising the same, thereby accomplishing the present invention.

Thus, the present invention is as follows.

<1> A compound represented by Formula (1) below,

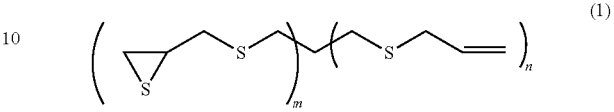

(wherein, m+n=4, m represents an integer of 0 to 3, and n represents an integer of 1 to 4).

<2> A composition for an optical material, comprising a compound represented by Formula (1) below and an episulfide compound other than the compound represented by Formula (1) below, wherein the proportion of the compound represented by Formula (1) below is 0.001-5.0 mass %,

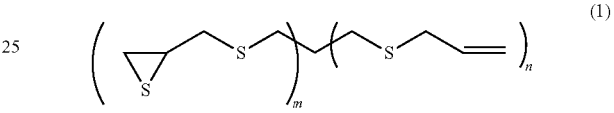

(wherein, m+n=4, m represents an integer of 0 to 3, and n represents an integer of 1 to 4).

<3> A method for producing an optical material, the method comprising a step of adding 0.0001-10 parts by mass of a polymerization catalyst relative to 100 parts by mass of the composition for an optical material according to <2> above, to allow polymerizing and curing.

<4> An optical material obtained by subjecting the composition for an optical material according to <2> above to polymerizing and curing.

<5> An optical lens comprising the optical material according to <4> above.

Advantageous Effect of the Invention

The present invention can provide an optical material with a high refractive index, which has enhanced dyeability without its heat resistance being deteriorated.

EMBODIMENTS FOR CARRYING OUT THE INVENTION

The present invention is a compound represented by Formula (1) below, and a composition for an optical material comprising the same.

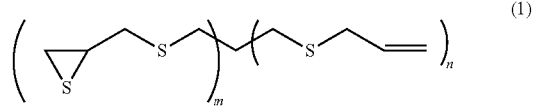

(wherein, m+n=4, m represents an integer of 0 to 3, and n represents an integer of 1 to 4).

Furthermore, while Formula (1) above comprise four kinds of compounds, namely, compounds wherein m=0 and n=4, m=1 and n=3, m=2 and n=2, and m=3 and n=1, respectively, it may represent either a single kind of compound or a mixture thereof at a certain ratio. From the viewpoint of the refractive index, it is preferably a compound wherein m=1 and n=3, m=2 and n=2, or m=3 and n=1, more preferably a compound wherein m=2 and n=2, or m=3 and n=1, and most preferably a compound wherein m=3 and n=1.

Hereinafter, a method for producing a compound represented by Formula (1) of the present invention will be described, although the production method is not particularly limited thereto. The compound represented by Formula (1) can be obtained by bringing an epoxy compound represented by Formula (2) below into reaction with a thia agent such as thiourea to obtain a reaction solution containing a compound represented by Formula (3) below, which is then treated with silica gel.

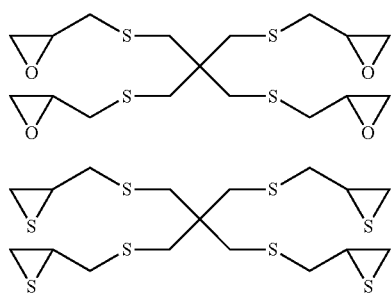

In the method of obtaining compounds represented by Formulae (1) and (3) through the above-described reaction, the thia agent such as thiourea is used in the theoretical amount, that is, an amount corresponding to epoxy of the epoxy compound represented by Formula (2) by mole, but if emphases are placed on the reaction rate and the purity, it can be used in the theoretical amount to an amount that is 2.5 times mole of the theoretical amount. Preferably, it is used in an amount that is 1.3-2.0 times mole of the theoretical amount, and more preferably in an amount that is 1.5-2.0 times mole of the theoretical amount. While examples of a polar organic solvent that can dissolve thiourea include alcohols such as methanol and ethanol, ethers such as diethyl ether, tetrahydrofuran and dioxane, and hydroxy ethers such as methyl cellosolve, ethyl cellosolve and butyl cellosolve, it is preferably an alcohol and most preferably methanol. While examples of a non-polar organic solvent that can dissolve the epoxy compound represented by Formula (2) include aliphatic hydrocarbons such as pentane, hexane and heptane, aromatic hydrocarbons such as benzene and toluene, and halogenated hydrocarbons such as dichloromethane, chloroform and chlorobenzene, it is preferably an aromatic hydrocarbon and most preferably toluene. While the solvents can be used at a volume ratio of polar organic solvent/non-polar organic solvent=0.1-10.0, it is preferably used at a volume ratio, polar organic solvent/non-polar organic solvent=0.2-5.0. If the volume ratio is less than 0.1, thiourea is poorly dissolved and thus the reaction proceeds insufficiently. On the other hand, if the volume ratio exceeds 10.0, polymer is significantly produced. The reaction is carried out at a temperature of 10° C.-30° C. If the temperature is lower than 10° C., the reaction rate is decreased and thiourea is poorly dissolved and thus the reaction proceeds insufficiently. On the other hand, if the temperature exceeds 30° C., polymer is significantly produced.

An acid or an acid anhydride is preferably added upon reaction, which is preferably acetic acid, propionic acid, butyric acid, succinic acid, maleic acid, benzoic acid, phthalic acid, pyromellitic acid, trimellitic acid, trifluoroacetic acid or an acid anhydride thereof, and most preferably acetic acid or an acid anhydride thereof. The amount added is usually in a range of 0.001-10 mass %, and preferably 0.01-5 mass %, relative to the total amount of the reaction solution. If the amount added is less than 0.001 mass %, polymer is significantly produced and the reaction yield is decreased, whereas if the amount added exceeds 10 mass %, the yield is significantly decreased.

A reaction solution containing the thus-obtained compound represented by Formula (3) above can be treated with silica gel to obtain a compound represented by Formula (1). Preferably, it is agitated with silica gel in a solvent such as toluene while increasing the temperature.

A compound represented by Formula (1) of the present invention can enhance dyeability while suppressing deterioration of heat resistance of a high refractive index resin. Preferably, the compound is made into a composition for an optical material with an episulfide compound other than the compound represented by Formula (1) so that an optical material obtained by subjecting the composition to polymerizing and curing can have enhanced dyeability.

Examples of the episulfide compound other than the compound represented by Formula (1) include a compound represented by Formula (3) above and a compound represented by Formula (4) below.

(wherein, m represents an integer of 0-4, and n represents an integer of 0-2).

While the followings are specific examples of the compound represented by Formula (4), the compound is not limited thereto.

Specifically, the examples include bis(β-epithiopropyl) sulfide (n=0 in Formula (4) above), bis(β-epithiopropyl) disulfide (m=0, n=1 in Formula (4) above), bis(β-epithiopropylthio)methane (m=1, n=1 in Formula (4) above), 1,2-bis(β-epithiopropylthio)ethane (m=2, n=1 in Formula (4) above), 1,3-bis(3-epithiopropylthio)propane (m=3, n=1 in Formula (4) above), 1,4-bis(β-epithiopropylthio)butane (m=4, n=1 in Formula (4) above), and bis(β-epithiopropylthioethyl)sulfide (m=2, n=2 in Formula (4) above).

Among them, the compound is preferably bis(β-epithiopropyl)sulfide (n=0 in Formula (4)) or bis(β-epithiopropyl) disulfide (m=0, n=1 in Formula (4)), and most preferably bis(β-epithiopropyl)sulfide (n=0 in Formula (4)).

The proportion of the compound represented by Formula (1) above in the composition for an optical material of the present invention is preferably 0.001-5.0 mass %, more preferably 0.005-3.0 mass % and particularly preferably 0.01-1.0 mass %. If the proportion of the compound represented by Formula (1) is below 0.001 mass %, the effect may not be adequate whereas if the proportion exceeds 5.0 mass %, the refractive index may be decreased.

If necessary, the composition for an optical material of the present invention may contain polythiol. Polythiol is a thiol compound that has two mercapto groups per molecule. Polythiol is effective in improving the color tone of the resin obtained from the composition for an optical material of the present invention upon heating.

While polythiol used in the present invention is not particularly limited, preferable examples thereof specifically include 1,2,6,7-tetramercapto-4-thiaheptane, methanedithiol, (sulfanyl methyl disulfanyl)methanethiol, bis(2-mercaptoethyl)sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, tetramercapto pentaerythritol, 1,3-bis(mercaptomethyl)benzene, 1,4-bis(mercaptomethyl)benzene and thiiranemethanethiol, for they are highly effective in improving the color tone, where polythiol is particularly preferably bis(2-mercaptoethyl)sulfide, 1,2,6,7-tetramercapto-4-thiaheptane, 1,2-bis(2-mercaptoethylthio)-3-mercaptopropane and 1,3-bis (mercaptomethyl)benzene, and most preferably 1,2,6,7-tetramercapto-4-thiaheptane. They are commercially available or can be synthesized according to a known method. Two or more kinds of them can also be used in combination.

In the composition for an optical material, the proportion of polythiol is preferably 0-25 mass % (for example, 0.1-25 mass %), more preferably 0-20 mass % (for example, 0.5-20 mass %), still more preferably 0-10 mass % (for example, 0.5-10 mass %) and particularly preferably 0-5 mass % (for example, 0.5-5 mass %) relative to the total amount of the composition.

If necessary, the composition for an optical material may contain sulfur and/or 1,2,3,5,6-pentathiepane. Sulfur and/or 1,2,3,5,6-pentathiepane are effective in enhancing the refractive index of the optical material (resin) obtained from the composition for an optical material of the present invention.

Any form of sulfur can be used in the present invention. Specifically, sulfur may be powdery sulfur, colloidal sulfur, precipitated sulfur, crystalline sulfur, sublimed sulfur or the like, where it is preferably powdery sulfur having fine particles from the viewpoint of the dissolution rate.

The particle size (diameter) of sulfur used in the present invention is preferably smaller than the mesh size of 10. If the particle size of sulfur is larger than the mesh size of 10, sulfur is difficult to be completely dissolved. The particle size of sulfur is more preferably smaller than the mesh size of 30 and most preferably smaller than the mesh size of 60.

The purity of sulfur used in the present invention is preferably 98% or higher, more preferably 99.0% or higher, still more preferably 99.5% or higher, and most preferably 99.9% or higher. If the purity of sulfur is 98% or more, the color tone of the resulting optical material can be further improved as compared to the case where the purity is lower than 98%.

Sulfur that satisfies the above-described conditions is readily available as a commercial product, and such product can favorably be used.

The method for obtaining 1,2,3,5,6-pentathiepane is not particularly limited. It may be a commercial product, it can be collected and extracted from a natural source such as crude oil, an animal or a plant, or it can be synthesized by a known method.

Examples of the synthesis method include the methods described in N. Takeda et al., Bull. Chem. Soc. Jpn., 68, 2757 (1995), F. Feher et al., Angew. Chem. Int. Ed., 7, 301 (1968), and G. W. Kutney et al., Can. J. Chem, 58, 1233 (1980).

The proportion of sulfur and/or 1,2,3,5,6-pentathiepane in the composition for an optical material is 0-40 mass % (for example, 1-40 mass %), preferably 0-30 mass % (for example, 5-30 mass %, 10-30 mass %), more preferably 0-25 mass % (for example, 5-25 mass %) and particularly preferably 0-20 mass % (for example, 5-20 mass %) relative to the total amount of the composition.

When the composition for an optical material of the present invention is polymerized/cured to obtain an optical material, a polymerization catalyst is preferably added. While an amine, phosphine or an onium salt can be used as the polymerization catalyst, it is preferably an onium salt, particularly, a quaternary ammonium salt, a quaternary phosphonium salt, a tertiary sulfonium salt or a secondary iodonium salt, more preferably a quaternary ammonium salt or a quaternary phosphonium salt which is highly compatible with the composition for an optical material, and still more preferably a quaternary phosphonium salt. More preferable examples of the polymerization catalyst include quaternary ammonium salts such as tetra-n-butylammonium bromide, benzyl triethyl ammonium chloride, cetyl dimethyl benzyl ammonium chloride and 1-n-dodecylpyridinium chloride, and quaternary phosphonium salts such as tetra-n-butylphosphonium bromide and tetraphenylphosphonium bromide. Among them, still more preferable polymerization catalysts are tetra-n-butylammonium bromide, benzyl triethyl ammonium chloride and tetra-n-butylphosphonium bromide.

While the amount of the polymerization catalyst added cannot be simply determined because it varies according to the components, the mixed ratio and the polymerizing and curing method of the composition, it is usually 0.0001-10 parts by mass, preferably 0.001-5 parts by mass, more preferably 0.01-1 parts by mass and most preferably 0.01-0.5 parts by mass relative to the total of 100 parts by mass of the composition for an optical material. If the amount of the polymerization catalyst added exceeds 10 parts by mass, polymerization takes place rapidly. On the other hand, if the amount of the polymerization catalyst added is less than 0.0001 parts by mass, the composition for an optical material may not be adequately cured and thus the heat resistance may be deteriorated.

Moreover, when an optical material is produced according to the method of the present invention, an additive such as a UV absorber, a blueing agent or a pigment can certainly be added to the composition for an optical material so as to further enhance practical use of the resulting optical material.

Preferable examples of the UV absorber are benzotriazole-based compound, where particularly preferable compounds are 2-(2-hydroxy-5-methylphenyl)-2H-benzotriazole, 5-chloro-2-(3,5-di-tert-butyl-2-hydroxyphenyl)-2H-benzotriazole, 2-(2-hydroxy-4-octylphenyl)-2H-benzotriazole, 2-(2-hydroxy-4-methoxyphenyl)-2H-benzotriazole, 2-(2-hydroxy-4-ethoxyphenyl)-2H-benzotriazole, 2-(2-hydroxy-4-butoxyphenyl)-2H-benzotriazole, 2-(2-hydroxy-4-octyloxyphenyl)-2H-benzotriazole, and 2-(2-hydroxy-5-t-octylphenyl)-2H-benzotriazole.

The amount of such a UV absorber added is usually 0.01-5 parts by mass relative to the total of 100 parts by mass of the composition for an optical material.

If necessary, a polymerization modifier can be added upon polymerizing/curing the composition for an optical material for the purposes of extending pot life, dispersing heat generated upon polymerization and else. Examples of the polymerization modifier include halides of Groups 13-16 of the extended periodic table. Among them, halides of silicon, germanium, tin and antimony are preferable, and chlorides of germanium, tin and antimony which have alkyl groups are more preferable. Still more preferable compounds are dibutyltin dichloride, butyltin trichloride, dioctyltin dichloride, octyltin trichloride, dibutyl dichlorogermanium, butyl trichlorogermanium, diphenyl dichlorogermanium, phenyl trichlorogermanium and triphenylantimony dichloride, and the most preferable compound is dibutyltin dichloride. One or more kinds of polymerization modifiers may be used alone or in combination.

The amount of the polymerization modifier added is 0.0001-5.0 parts by mass, preferably 0.0005-3.0 parts by mass and more preferably 0.001-2.0 parts by mass relative to the total of 100 parts by mass of the composition for an optical material. If the amount of the polymerization modifier added is less than 0.0001 parts by mass, adequate pot life of the resulting optical material is not ensured, whereas if the amount of the polymerization modifier added exceeds 5.0 parts by mass, the composition for an optical material is not adequately cured and thus the heat resistance of the resulting optical material may be deteriorated The thus-obtained composition for an optical material can be poured into a frame such as a mold and polymerized to give an optical material.

From the viewpoint of enhancing the quality of the optical material of the present invention, impurities are preferably filtrated and removed with a filter or the like having a pore size of about 0.1-5 μm upon pouring the composition for an optical material of the present invention into a frame.

The composition for an optical material of the present invention is polymerized generally as follows. Specifically, the curing time is usually 1-100 hours, and the curing temperature is usually −10° C.-140° C. Polymerization takes place through a step of maintaining a predetermined polymerization temperature for a predetermined time, a step of increasing the temperature by 0.1° C.-100° C./h, and a step of decreasing the temperature by 0.1° C.-100° C./h, or through a combination of these steps.

Furthermore, after the curing process, the resulting optical material is preferably annealed at a temperature of 50-150° C. for about 10 minutes to about 5 hours so as to remove distortion of the optical material of the present invention. If necessary, the resulting optical material may further be subjected to a surface treatment such as dyeing, hard coating, impact-resistant coating, anti-reflection treatment, anti-fog treatment or the like.

The optical material of the present invention can favorably be used as an optical lens.

EXAMPLES

Hereinafter, the content of the present invention will be described by means of examples and comparative examples, although the present invention should not be limited to the following examples. The optical materials obtained according to the methods described in the examples and the comparative examples below were evaluated by the following methods.

Refractive index: Abbe refractometer NAR-4T available from Atago Co., Ltd. was used to measure the refractive index at the e-line at 25° C.

Heat resistance: A sample was cut out to have a thickness of 3 mm, a load of 50 g was placed onto a 0.5-mmφ pin and the temperature was increased at 10° C./min. to perform TMA measurement (TMA/SS6100 available from Seiko Instruments Inc.). Evaluation was conducted based on the peak temperature of DTMA, i.e., the curve of differential temperature of the acquired TMA curve, and the DTMA peak value.

The lower this DTMA peak value is, the less softening due to heat is likely to be caused and therefore evaluated to have higher heat resistance. In particular, if the peak value is negative or no peak is observed, softening point was considered to be absent. Those with a DTMA peak value of 1.0 or less were grouped A, those with a DTMA peak value exceeding 1.0 but 1.5 or less were grouped B, and those with a DTMA peak value exceeding 1.5 were grouped C. "C" was considered to be a failure level.

Dyeability: 2 g of Seiko Plax Diacoat Brown D, 3 g of Seiko Plax dyeing auxiliary and 20 g of benzyl alcohol were added to 1 L of water, and the temperature was increased to 90° C. The optical material was immersed in this for 15 minutes to determine the total light transmittance. Those with transmittance of less than 30% was grouped "A", those with transmittance of 30% or more but less than 70% were grouped "B", and those with transmittance of 70% or more were grouped "C". The lower the transmittance, the better the dyeability is. "A" and "B" are acceptable but "A" is more favorable. "C" is a failure level.

Example 1

100 mL of toluene, 100 mL of methanol, 1.24 g (0.012 mol) of acetic anhydride and 30.5 g (0.40 mol) of thiourea were added to 20.1 g (0.047 mol) of tetrakis(β-epoxypropylthio methyl)methane, and the mixture was stirred at 30° C. for 24 hours. Subsequently, 400 mL of toluene and 400 mL of 5% sulfuric acid were added, and the toluene layer was washed with water for three times to give a toluene layer containing tetrakis(β-epithiopropylthiomethyl)methane. 100 g of silica gel was fed to the obtained toluene layer and the resultant was stirred at 40° C. for 24 hours. Silica gel was removed by filtration and toluene was distilled away. The residue left after distilling away toluene was separated in a silica gel column using chloroform, toluene and hexane as developing solvents to obtain a compound represented by Formula (1) (ratio of the following Compound a, Compound b, Compound c and Compound d was a:b:c:d=2:3:3:2).

Hereinbelow, the compound represented by Formula (1) used in Examples 2-9 refers to this compound synthesized in Example 1.

$m=0$ and $n=4$ (hereinafter, "Compound a")
$^1$H-NMR (CDCl$_3$): 2.36 ppm (8H), 3.11 ppm (81H), 5.03 ppm (4H), 5.12 ppm (4H), 5.96 ppm (41H)
$^{13}$C-NMR (CDCl$_3$): 36.9 ppm (4C), 38.3 ppm (4C), 39.3 ppm (1C), 115.9 ppm (4C), 132.7 ppm (4C)

$m=1$ and $n=3$ (hereinafter, "Compound b")
$^1$H-NMR (CDCl$_3$): 2.23 ppm (21H), 2.36 ppm (811), 2.77 ppm (2H), 2.54 ppm (1H), 3.11 ppm (6H), 5.03 ppm (3H), 5.12 ppm (3H), 5.96 ppm (3H)
$^{13}$C-NMR (CDCl$_3$): 24.8 ppm (1C), 33.0 ppm (1C), 36.9 ppm (3C), 37.8 ppm (1C), 38.3 ppm (3C), 39.2 ppm (1C), 44.8 ppm (1C), 115.9 ppm (3C), 132.7 ppm (3C)

$m=2$ and $n=2$ (hereinafter, "Compound c")
$^1$H-NMR (CDCl$_3$): 2.23 ppm (4H), 2.36 ppm (8H), 2.77 ppm (4H), 2.54 ppm (2H), 3.11 ppm (4H), 5.03 ppm (211), 5.12 ppm (2H), 5.96 ppm (2H)
$^{13}$C-NMR (CDCl$_3$): 24.8 ppm (2C), 33.0 ppm (2C), 36.9 ppm (2C), 37.8 ppm (2C), 38.3 ppm (2C), 39.1 ppm (1C), 44.8 ppm (2C), 115.9 ppm (2C), 132.7 ppm (2C)

$m=3$ and $n=1$ (hereinafter, "Compound d")
$^1$H-NMR (CDCl$_3$): 2.23 ppm (6H), 2.36 ppm (811), 2.77 ppm (6H), 2.54 ppm (3H), 3.11 ppm (2H), 5.03 ppm (1H), 5.12 ppm (1H), 5.96 ppm (1H)
$^{13}$C-NMR (CDCl$_3$): 24.8 ppm (3C), 33.0 ppm (3C), 36.9 ppm (1C), 37.8 ppm (3C), 38.3 ppm (2C), 39.0 ppm (1C), 44.8 ppm (3C), 115.9 ppm (1C), 132.7 ppm (1C)

Example 2

0.01 parts by mass of the compound represented by Formula (1) (ratio of Compounds a, b, c and d was a:b:c:d=2:3:3:2) and 0.05 parts by mass of tetra-n-butylphosphonium bromide as a polymerization catalyst were added to 99.99 parts by mass of tetrakis(β-epithiopropylthiomethyl)methane (a compound represented by Formula (3)), and then the mixture was thoroughly mixed to achieve a homogeneous mixture. Then, deaeration was performed at a vacuum degree of 1.3 kPa and the mixture was poured into a mold formed of two pieces of glass and tape. The resultant was heated at 30° C. for 10 hours, then the temperature was increased to 100° C. at a constant rate by spending 10 hours, and finally heating was conducted at 100° C. for an hour to allow polymerizing and curing. After cooling, the resultant was released from the mold, and annealed at 120° C. for 30 minutes to obtain a molded plate. The refractive index and the dyeability of the resulting optical material were evaluated. The results from the evaluations are shown in Table 1.

Examples 3-9, Comparative Examples 1 and 2

Molded plates were obtained in the same manner as Example 2 except the compositions were as indicated in Table 1. The results from the evaluations are shown in Table 1.

TABLE 1

| Example | Compound represented by Formula (3) (parts by mass) | Compound represented by Formula (1) (parts by mass) | Compound (e) (parts by mass) | Refractive index | Heat resistance | Dyeability |
|---|---|---|---|---|---|---|
| Example 2 | 99.99 | 0.01 | — | 1.72 | A | B |
| Example 3 | 99.90 | 0.1 | — | 1.72 | A | A |
| Example 4 | 99.00 | 1.0 | — | 1.71 | A | A |
| Example 5 | 95.00 | 5.0 | — | 1.69 | A | A |
| Comparative example 1 | 100.00 | — | — | 1.72 | A | C |
| Example 6 | 96.99 | 0.01 | 3.0 | 1.72 | A | B |
| Example 7 | 96.90 | 0.1 | 3.0 | 1.72 | B | A |
| Example 8 | 96.00 | 1.0 | 3.0 | 1.69 | B | A |
| Example 9 | 92.00 | 5.0 | 3.0 | 1.69 | B | A |
| Comparative example 2 | 97.00 | — | 3.0 | 1.70 | B | C |

Compound (e): 1,2,6,7-tetramercapto-4-thiaheptane

Example 10

A toluene layer containing tetrakis(β-epithiopropylthiomethyl)methane was obtained in the same manner as Example 1. 100 g of silica gel was fed to the obtained toluene layer and the resultant was stirred at 40° C. for 48 hours. Silica gel was removed by filtration and toluene was distilled away. The residue left after distilling away toluene was separated in a silica gel column using chloroform, toluene and hexane as developing solvents to obtain a compound represented by Formula (1) (ratio of the following Compound a, Compound b, Compound c and Compound d was a:b:c:d=0:1:3:6).

Hereinbelow, the compound represented by Formula (1) used in Examples 11-14 refers to this compound synthesized in Example 10.

Example 11

0.01 parts by mass of the compound represented by Formula (1) (ratio of Compounds a, b, c and d was a:b:c:d=0:1:3:6) and 0.05 parts by mass of tetra-n-butylphosphonium bromide as a polymerization catalyst were added to 99.99 parts by mass of bis(β-epithiopropyl)sulfide (a compound represented by Formula (4), wherein n=0), and then the mixture was thoroughly mixed to achieve a homogeneous mixture. Then, deaeration was performed at a vacuum degree of 1.3 kPa and the mixture was poured into a mold formed of two pieces of glass and tape. The resultant was heated at 30° C. for 10 hours, then the temperature was increased to 100° C. at a constant rate by spending 10 hours, and finally heating was conducted at 100° C. for an hour to allow polymerizing and curing. After cooling, the resultant was released from the mold, and annealed at 120° C. for 30 minutes to obtain a molded plate. The refractive index and the dyeability of the resulting optical material were evaluated. The results from the evaluations are shown in Table 2.

Examples 12-14, Comparative Example 3

Molded plates were obtained in the same manner as Example 11 except the compositions were as indicated in Table 2. The results from the evaluations are shown in Table 2.

TABLE 2

| Example | Compound represented by Formula (4) (parts by mass) | Compound represented by Formula (1) (parts by mass) | Refractive index | Heat resistance | Dyeability |
|---|---|---|---|---|---|
| Example 11 | 99.99 | 0.01 | 1.71 | A | B |
| Example 12 | 99.90 | 0.1 | 1.71 | A | A |
| Example 13 | 99.00 | 1.0 | 1.70 | A | A |
| Example 14 | 95.00 | 5.0 | 1.67 | A | A |
| Comparative example 3 | 100.00 | — | 1.71 | A | C |

The invention claimed is:

1. A composition for an optical material, comprising a compound represented by Formula (1) below and an episulfide compound other than the compound represented by Formula (1) below, wherein the proportion of the compound represented by Formula (1) below is 0.001-5.0 mass %,

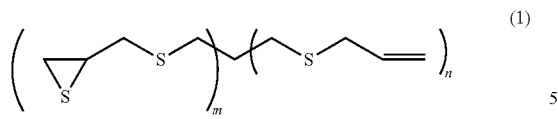

wherein, m+n=4, m represents an integer of 0 to 3, and n represents an integer of 1 to 4.

2. A method for producing an optical material, the method comprising adding 0.0001-10 parts by mass of a polymerization catalyst relative to 100 parts by mass of the composition for an optical material according to claim 1, to allow polymerizing and curing.

3. An optical material obtained by subjecting the composition for an optical material according to claim 1 to polymerizing and curing.

4. An optical lens comprising the optical material according to claim 3.

\* \* \* \* \*